US008603434B2

(12) United States Patent
Hurst et al.

(10) Patent No.: US 8,603,434 B2
(45) Date of Patent: Dec. 10, 2013

(54) BINDER-CONVERTED ALUMINOSILICATE X-TYPE ZEOLITE COMPOSITIONS WITH LOW LTA-TYPE ZEOLITE

(75) Inventors: Jack E. Hurst, Mobile, AL (US); Linda S. Cheng, Highland Park, IL (US); Robert W. Broach, Deerfield, IL (US)

(73) Assignee: UOP LLC, Des Plaines, IL (US)

( * ) Notice: Subject to any disclaimer, the term of this patent is extended or adjusted under 35 U.S.C. 154(b) by 2 days.

(21) Appl. No.: 13/426,970

(22) Filed: Mar. 22, 2012

(65) Prior Publication Data

US 2012/0264993 A1    Oct. 18, 2012

Related U.S. Application Data

(60) Provisional application No. 61/474,927, filed on Apr. 13, 2011.

(51) Int. Cl.
*C01B 39/46* (2006.01)
*C01B 39/22* (2006.01)
*B01J 29/80* (2006.01)
*C01B 39/02* (2006.01)
*B01J 29/82* (2006.01)

(52) U.S. Cl.
CPC ............ *C01B 39/023* (2013.01); *C01B 39/22* (2013.01); *C01B 39/46* (2013.01); *B01J 29/80* (2013.01); *B01J 29/82* (2013.01); *B01J 2229/42* (2013.01)
USPC .................. 423/718; 502/67; 502/71; 502/79

(58) Field of Classification Search
USPC .................................. 423/718; 502/67, 71, 79
See application file for complete search history.

(56) References Cited

U.S. PATENT DOCUMENTS

| 2,882,244 | A | * | 4/1959 | Milton | 423/718 |
| 4,818,508 | A |   | 4/1989 | Flank |  |
| 7,812,208 | B2 |   | 10/2010 | Cheng |  |
| 7,820,869 | B2 | * | 10/2010 | Priegnitz et al. | 585/827 |
| 8,283,274 | B2 | * | 10/2012 | Cheng et al. | 502/75 |
| 8,431,764 | B2 | * | 4/2013 | Hurst et al. | 585/831 |

FOREIGN PATENT DOCUMENTS

JP    5163015 A    6/1993

OTHER PUBLICATIONS

U.S. Appl. No. 13/426,955, filed Mar. 22, 2012, Hurst et al.
U.S. Appl. No. 13/426,979, filed Mar. 22, 2012, Hurst et al.
Breck, Manufacture and Properties of Commercial Molecular Sieve Adsorbents, Zeolite Molecular Sieves, 1974, John Wiley & Sons, Inc., ISBN 0-471-09985-6, pp. 725-755.

* cited by examiner

*Primary Examiner* — David M Brunsman
(74) *Attorney, Agent, or Firm* — Kurt D. Van Tassel

(57) ABSTRACT

A zeolitic binder-converted composition comprising (a) a zeolite X composition having at least a first zeolite X having a mean diameter not greater than 2.7 microns, and a second zeolite X, wherein the second zeolite X is obtained by converting a binder material to the second zeolite X and the binder material is in a range from 5 to 50 wt % of the zeolite X composition; and (b) an unconverted binder material content, after conversion to the second zeolite X is complete, in a range from 0 to 3 wt % of the zeolite X composition. The zeolite X composition has an average Si/Al framework mole ratio in a range from 1.0 to 1.5, and a relative LTA intensity not greater than 1.0, as determined by x-ray diffraction (XRD).

7 Claims, 2 Drawing Sheets

BINDER-CONVERTED ALUMINOSILICATE X-TYPE ZEOLITE COMPOSITIONS WITH LOW LTA-TYPE ZEOLITE

CROSS-REFERENCE TO RELATED APPLICATION

This application claims benefit of U.S. Provisional Application No. 61/474,927 filed on Apr. 13, 2011.

FIELD OF THE INVENTION

This invention relates to a new binder-converted composition derived from a new family of X-type aluminosilicate zeolites. More specifically, this new binder-converted composition is made using X-type zeolites having either low or no detectable levels of LTA-type zeolite, as determined by x-ray diffraction, and binder material convertible to X-type zeolite.

BACKGROUND OF THE INVENTION

Zeolites are crystalline aluminosilicate compositions that are microporous and that are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and their ability to adsorb and reversibly desorb an adsorbed phase that is dispersed throughout the internal voids of the crystal without significantly displacing any atoms that make up the permanent zeolite crystal structure.

Among other uses, zeolites can be used to make an adsorbent material. In adsorbent materials, zeolites can separate components of either multi-component gas mixtures or liquid mixtures. It's generally understood that the presence of an inert or non-reactive zeolite ("contaminant zeolite") can even diminish the adsorption performance of certain zeolites. Conventionally, however, the presence of some relatively low, but still tolerable, concentration of a contaminant zeolite has been viewed as commercially acceptable since it's generally considered to produce an insignificant loss or drop in the finished adsorbent's performance. Accordingly, there's a diminishing point of return in further reducing contaminant zeolite levels. So conventionally, it's been considered more cost-effective to leave contaminant zeolite(s) mixed with the active zeolite, than to remove or further reduce the contaminant zeolite in light of its related adsorbent's projected performance.

Accordingly, there is a need for a zeolite with improved purity, more particularly an X type zeolite that can have a more beneficial effect on the zeolite's process performance than expected for the extent to which the contaminant zeolite content is either further reduced, beyond customary levels, or fully removed.

Despite this conventional view, however, Applicants have discovered and successfully made a zeolite with little to no detectable amounts of a particular contaminant zeolite, namely, a LTA-type zeolite (hereinafter "LTA zeolite"). More specifically, Applicants have discovered and made a form of zeolite X with either little or no detectable LTA zeolite ("low LTA-containing X zeolite"), as determined by the x-ray diffraction ("XRD") method described below, which also has a particle size not greater than 2.7 microns (μm), as determined by the sedigraph analysis described below. Applicants have also discovered that a low LTA-containing X zeolite is useful for making a zeolitic binder-converted composition (discussed below).

One adsorbent application of interest, among others, relates to separating para-xylene (pX) from a mixture of xylenes in a fixed bed process, which is often a simulated moving bed (SMB) adsorption process.

The SMB adsorption process is used commercially in a number of large scale petrochemical separations to recover high purity pX from mixed xylenes. As used herein, "mixed xylenes" refers to a mixture of $C_8$ aromatic isomers that includes ethyl benzene (EB), pX, meta-xylene (mX) and ortho-xylene (oX). High purity pX is used for the production of polyester fibers, resins and films. Typically, pX is converted to terephthalic acid (TPA) or dimethyl terephthalate (DMT), which is then reacted with ethylene glycol to form polyethylene terephthalate (PET), the raw material for most polyesters.

The general technique employed in the performance of SMB adsorptive separation processes is widely described and practiced. Generally, the process simulates a moving bed of adsorbent with continuous counter-current flow of a liquid feed over the adsorbent. Feed and products enter and leave adsorbent beds continuously, at nearly constant compositions. Separation is accomplished by exploiting the differences in affinity of the adsorbent for pX relative to the other $C_8$ aromatic isomers.

Typical adsorbents used in SMB adsorption processes generally include crystalline aluminosilicate zeolites and can comprise both the natural and synthetic aluminosilicates. Suitable crystalline aluminosilicate zeolites for use as an adsorbent selective for pX include those having aluminosilicate cage structures in which alumina and silica tetrahedra are intimately connected with each other in an open three dimensional crystalline network. The tetrahedra are cross linked by shared oxygen atoms, with spaces between the tetrahedra occupied by water molecules prior to partial or total dehydration of the zeolite. The dehydration results in crystals interlaced with channels having molecular dimensions.

In a hydrated form the crystalline aluminosilicate zeolites are generally represented by the formula:

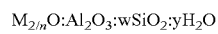

$$M_{2/n}O:Al_2O_3:wSiO_2:yH_2O$$

where "M" is a cation that balances the electrovalence of the tetrahedra and is generally referred to as an exchangeable cationic site, "n" represents the valence of the cation, "w" represents the moles of $SiO_2$, and "y" represents the moles of water. Such crystalline aluminosilicate zeolites that find use as an adsorbent possess relatively well-defined pore structures. The exact type aluminosilicate zeolite is generally identified by the particular silica:alumina molar ratio and the pore dimensions of the cage structures.

Cations (M) occupying exchangeable cationic sites in the zeolitic adsorbent may be replaced with other cations by ion exchange methods well known to those having ordinary skill in the field of crystalline aluminosilicates. Crystalline aluminosilicates, such as zeolite X with barium and potassium cations at the exchangeable cationic sites within the zeolite, are known to selectively adsorb pX in a mixture comprising at least one other $C_8$ aromatic isomer beyond pX.

Generally, zeolitic adsorbents used in separation processes contain the zeolitic crystalline material dispersed in an amorphous material or inorganic matrix having channels and cavities that enable liquid access to the crystalline material. Silica, alumina or certain clays and mixtures thereof are typical of such inorganic matrix materials, which act as a "binder" to form or agglomerate the zeolitic crystalline particles that otherwise would comprise a fine powder. Agglomerated zeolitic adsorbents may thus be in the form of extrudates, aggregates, tablets, macrospheres such as beads, granules, or the like.

The binder is typically inert and contributes little, if any, to the adsorptive separation process. Efforts to improve adsorbent efficacy generally have focused on (a) decreasing the size of the zeolite particles forming the adsorbent and (b) increasing the zeolite volume (i.e., the active separation component) within adsorbents. One method for increasing the zeolite volume in the adsorbent is to convert the binder into zeolite in a conversion process referred to as "zeolitization," while preferably maintaining or improving the adsorbent material's strength and macroporosity, among other things. This binder-conversion process thereby obtains a zeolitic binder-converted composition, which is often referred to as a "binderless" zeolitic adsorbent. However, the description of "binderless" does not necessarily mean all original binder material is converted to zeolitic material since some small fraction of binder material (e.g., up to 3 wt %) may not be converted, depending on various factors, such as, original binder content, zeolitization conditions, etc. While a binder-conversion process has resulted in improved adsorbent efficacy, still further improvements in adsorptive separation process efficiency are desired.

Accordingly, an improved zeolitic binder-converted adsorbent composition obtained from a X zeolite with improved purity—more specifically, a low LTA-containing X zeolite having a particle size not greater than 2.7 μm—to recover high purity pX from mixed xylenes in a liquid-phase separation process using the zeolitic binder-converted adsorbent is described more fully herein. A method for obtaining a low LTA-containing X zeolite having a particle size not greater than 2.7 μm is also described herein, as well as a method for obtaining a zeolitic binder-converted adsorbent using such a low LTA-containing X.

Furthermore, other desirable features and characteristics of the present invention will become apparent from the subsequent detailed description of the invention and the appended claims.

SUMMARY OF THE INVENTION

According to one aspect of the invention, there is provided a zeolitic binder-converted composition comprising:
(a) a zeolite X composition having at least a first zeolite X having a mean diameter not greater than 2.7 microns, as determined by sedigraph analysis, and a second zeolite X, wherein the second zeolite X is obtained by converting a binder material to the second zeolite X and the binder material is in a range from 5 to 30 wt % of the zeolite X composition, and
(b) an unconverted binder material content, after conversion to the second zeolite X is complete, in a range from 0 to 3 wt % of the zeolite X composition; wherein the zeolite X composition has
(i) an average Si/Al framework mole ratio in a range from 1.0 to 1.5, wherein the Si/Al framework mole ratio of the first zeolite and the second zeolite may be the same or different; and (ii) a relative LTA intensity not greater than 1.0, as determined by a x-ray diffraction (XRD) method using a source of CuKα radiation to obtain XRD intensities in range from 5° to 25° 2θ,
wherein, the relative LTA intensity is calculated as 100 times the quotient of $$\frac{\text{a sample } LTA \text{ XRD intensity for the zeolite } X}{\text{a reference } XRD \text{ intensity for a } LTA \text{ zeolite reference material consisting essentially of } LTA \text{ zeolite}}$$

wherein,
(1) the sample LTA XRD intensity of the zeolite X composition is the sum of the intensities for each LTA peak with Miller indices of (2 0 0), (4 2 0), and (6 2 2) at 7.27±0.16°, 16.29±0.34° and 24.27±0.50° 2θ, and
(2) the reference XRD intensity of the LTA-type zeolite reference material is the sum of the intensities for each LTA peak with Miller indices of (2 0 0), (4 2 0), and (6 2 2) at 7.27±0.16°, 16.29±0.34° and 24.27±0.50° 2θ,
wherein,
the sample LTA XRD intensity and the reference XRD intensity are each
(a) obtained for a sodium-exchanged form of the zeolite X composition and the LTA-type zeolite reference material, respectively, and
(b) equilibrated at 50% relative humidity.

DETAILED DESCRIPTION OF THE INVENTION

Figure 1:
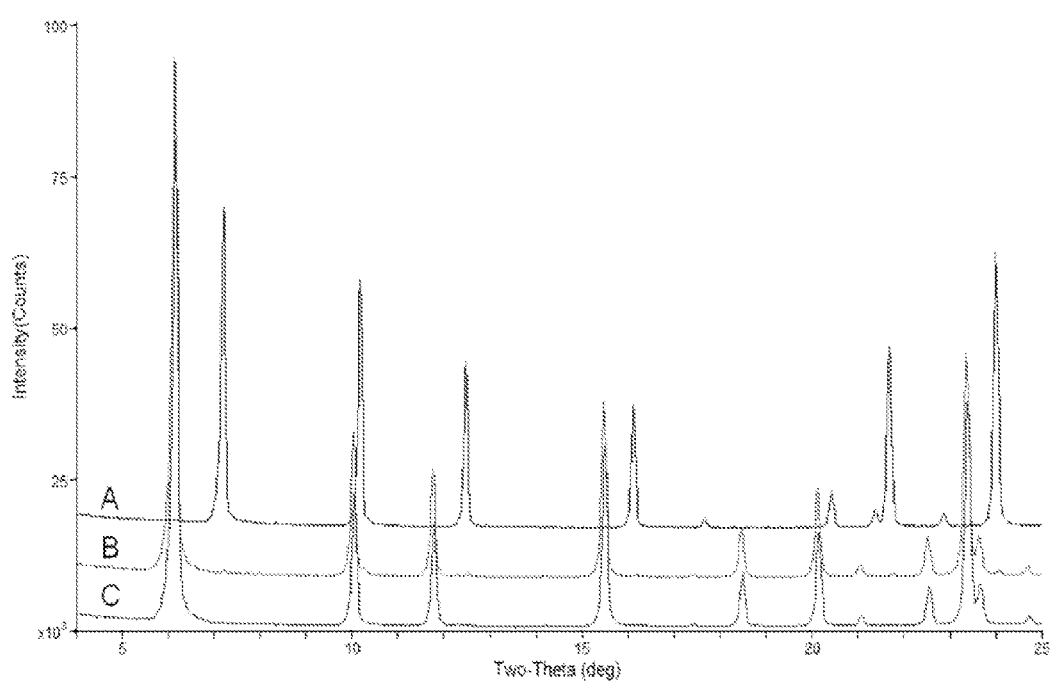
FIG. 1 shows 3 XRD scans providing three LTA zeolite peaks with their respective Miller indices and 2θ values, which can be used for determining the LTA zeolite content of different sample materials, wherein scan A is a XRD scan of a reference material, a Na-exchanged zeolite A; scan B is an XRD scan of a comparative material, prepared in accordance with the synthesis example (C-1) but fully Na-exchanged prior to XRD analysis, and scan C is an XRD scan of a low-LTA containing X zeolite indicating no detectable LTA zeolite, also fully Na-exchanged prior to XRD analysis.

Applicants have prepared a zeolitic binder-converted composition produced with a zeolite having a low or no detectable LTA zeolite content.

Zeolite X Preparation

The structure of zeolite X is described in detail in U.S. Pat. No. 2,882,244. A low LTA-containing X zeolite, as determined by the XRD method described below, having a particle size not greater than 2.7 μm, as determined by the sedigraph analysis described below, can be prepared, for example, using either a zeolite seed material or initiator material. Zeolite particle size is sometimes referred to in the art as crystallite size, but for consistency particle size will be used herein.

Smaller zeolite particle sizes can be obtained using a seed or initiator material for initiating zeolite crystallite growth (sometimes described as nucleation). So a seed or initiator material is first prepared and then blended into a gel composition at a gel composition to initiator ratio to obtain a zeolite particle size in a targeted range. The ratio of gel composition to seed or initiator material governs the relative number or concentration of nucleation sites, which in turn affects the particle size obtained for the zeolite X. Generally, higher concentrations of seed or initiator material reduce the particle size. For example, zeolite X preparations having mean diameter in a range from 2.7 microns to 0.5 microns can be made using gel to seed/initiator ratios in a range from 7900 to 1 and 85 to 1, by weight, respectively. In view of the present disclosure, those having skill in the art can readily vary the gel to seed or initiator weight ratios to obtain any average zeolite particle size not greater than 2.7μm.

A typical gel composition comprises $Na_2O$, $SiO_2$, $Al_2O_3$, and water. The Applicants have found that, generally, as the amount of $Na_2O$ used relative to the other gel or initiator components (i.e., $SiO_2$, $Al_2O_3$, $H_2O$) is increased, the mean diameter of the zeolite X obtained is reduced. However, as the amount of $Na_2O$ in the gel or initiator composition increases, there is an increased tendency to produce contaminant LTA zeolite. Also, when an increased concentration of $Na_2O$ is used relative to $SiO_2$ and $Al_2O_3$, the ratio of $SiO_2$ to $Al_2O_3$ is effectively reduced, which in turn obtains a lower Si/Al framework ratio in the zeolite when a seed or initiator material is used to make the X zeolite. But generally, a lower Si/Al framework ratio results in a larger zeolite framework unit cell size (UCS), which in turn can adversely affect the zeolite's selectivity for certain species of interest. Accordingly, while obtaining smaller particle size by increasing the $Na_2O$ concentration can be beneficial, at the same time it can create other undesired attributes, such as formation of contaminant LTA zeolite and a larger UCS.

Interestingly, if an initiator or seed material is not used to make the zeolite X, the smallest obtainable mean diameter is 3 μm, even when the total $Na_2O$, $SiO_2$ and $Al_2O_3$ molar ratios are substantially the same or similar to those for a synthesis using an initiator or seed material.

Applicants have surprisingly discovered how to produce a Zeolite X with decreased UCS, while producing little to no detectable LTA zeolite in the formation of Zeolite X. Total mole ratios for primary reactants relative to $Al_2O_3$, including seed or initiator material contributions, for a small particle, low LTA-containing X zeolite are provided below.

| Small Particle, Low LTA-containing X Zeolite with Initiator Range | $Na_2O$ | $SiO_2$ | $Al_2O_3$ | $H_2O$ |
|---|---|---|---|---|
| Broad | 3.94-4.05 | 2.96-3.34 | 1.00 | 200.1-202.8 |
| Preferred | 3.99-4.02 | 3.15-3.24 | 1.00 | 201.5-202.1 |
| Example S-1 & S-2 | 4.02 | 3.24 | 1.00 | 202.1 |

For comparative purposes, the typical mole ratios for a conventional small particle, high LTA-containing X zeolite synthesis for primary reactants relative to $Al_2O_3$, including seed or initiator material contributions are provided below.

| Small Particle, High LTA-containing X Zeolite with Initiator Range | $Na_2O$ | $SiO_2$ | $Al_2O_3$ | $H_2O$ |
|---|---|---|---|---|
| Broad | 3.86-3.93 | 2.70-2.95 | 1.00 | 198.3-200.1 |
| Example C-1 | 3.93 | 2.95 | 1.00 | 200.1 |

For comparative purposes, the typical mole ratios for a conventional large particle (i.e., >3 μm mean diameter), low LTA-containing X zeolite synthesis without initiator for primary reactants relative to $Al_2O_3$ are provided below.

| Large Particle, Low LTA-containing X Zeolite without Initiator Range | $Na_2O$ | $SiO_2$ | $Al_2O_3$ | $H_2O$ |
|---|---|---|---|---|
| Broad | 2.50-4.26 | 2.77-3.01 | 1.00 | 65-240 |
| Example C-2 | 2.63 | 2.83 | 1.00 | 79.9 |

As noted above, the smallest mean diameter obtainable for an X zeolite made without an initiator or seed material is 3 μm. And although such a large particle zeolite X tends to have a low LTA content, it cannot obtain a mean diameter below 3 μm without an initiator or seed material, which inevitably leads to producing an undesirably high LTA content, absent Applicant's newly discovered process for making a low LTA-containing X zeolite with a mean diameter not greater than 2.7 μm.

Gel Composition

A gel composition may be prepared by combining a gel makeup solution with an aluminate makeup solution containing, for example, about 12% alumina by weight. The gel makeup solution is prepared by mixing water, caustic solution, and sodium silicate, and cooling the mixture to about 38° C. (100° F.). The aluminate makeup solution is prepared by dissolving alumina trihydrate in a caustic solution, with heating as necessary for dissolution, followed by cooling and aging at about 38° C. (100° F.) prior to combining it with the gel makeup solution. The gel makeup solution and aluminate solution are then combined under vigorous agitation for a short period (e.g., about 30 minutes), prior to adding the required amount of seed.

Seed Material Preparation

The seed is prepared in a similar manner to the gel composition. A typical seed composition therefore also comprises $Na_2O$, $SiO_2$, $Al_2O_3$, and water. For each mole of $Al_2O_3$, about 10-20 moles of $Na_2O$ and $SiO_2$, and about 150-500 moles of water, can be used. The aluminate solution used in preparing the seed may contain, for example, about 18% alumina by weight. After the gel composition and seed are combined, the mixture is heated while agitation is maintained, and then aged under agitated conditions for a time from about 5 to about 50 hours and at a temperature from about 25° C. (75° F.) to about 150° C. (300° F.) to achieve the desired crystallite formation from the seed nuclei. The resulting solid material can then be filtered, washed, and dried to obtain a small particle size zeolite X. The particle size of the zeolite X is determined by the sedigraph analysis, as described more fully under the characterization examples section below.

Binder

Zeolite X is used in the synthesis of a binder-converted composition by combining the first "prepared" or already made zeolite X with a zeolite X-precursor. The preferred zeolite X-precursors include clays that will obtain a Si/Al framework ratio in a range from 1 to 1.5 and preferably, a Si/Al framework ratio substantially consistent with the preferred Si/Al ratio in a range from 1.15 to 1.35 for the original low LTA-containing X zeolite before clay conversion. More preferably, the zeolite X-precursors are clays such as kaolin, kaolinites, and halloysite. The zeolite X-precursors are used to make a second zeolite X in a binder-converted composition.

Preferably, the mean particle diameter of the binder material is in a range from 0.4 to 4.6 μm.

The forming procedure involves combining the zeolite X-precursor, exemplified by kaolin clay, with the zeolite X powder of the prepared first zeolite X and optionally other additives such as pore-generating materials (e.g., corn starch to provide macroporosity) and water as needed to obtain the proper consistency for shaping. Shaping or forming into larger beads, spheres, pellets, etc., can be performed using conventional methods including bead forming processes such as Nauta mixing, tumbling, or drum rolling to prepare larger particles (e.g., in the range of about 16-60 Standard U.S. Mesh size). The formed particles comprising the prepared first zeolite X and the zeolite X-precursor are then activated at a temperature generally ranging from about 500° C. to about 700° C. (about 930° F. to about 1300° F.). In the case of a zeolite X-precursor comprising kaolin clay, activation causes this material to undergo endothermic dehydroxylation, whereby the disordered, meta-kaolin phase is formed.

Following activation, caustic digestion of the formed particles (e.g., using sodium hydroxide), then converts the activated zeolite X-precursor into a second zeolite X, resulting in a binder-converted composition that may comprise or consist essentially of zeolite X, with low or no detectable LTA zeolite content.

The Si/Al framework ratio of the converted portion of zeolite X, as well as the contribution of this material in the final formulation, may be varied according to the type and amount of zeolite X-precursor that is incorporated into the formed particles. Normally, the Si/Al ratio of the zeolite X-precursor will be substantially conserved upon conversion into zeolite X. Thus, a typical kaolin clay having a Si/Al ratio in a range from 1.0 to 1.1 will convert to a zeolite X portion having a zeolite framework ratio within this range. It is possible, therefore, to prepare binder-converted compositions having first (prepared) and second (converted) portions of zeolite X with differing Si/Al ratios.

However, increasing the Si/Al framework ratio of zeolite X, from a range of 1.0 to 1.1 to a range from 1.05 to 1.35, can result in increased desorbent strength (e.g., with para-diethylbenzene (pDEB) desorbent) in the adsorptive separation of pX. When zeolite X having a Si/Al framework ratio of 1.0 is substituted for higher ratio zeolite X in the adsorbent formulation, the pDEB desorbent strength is reduced considerably (i.e., the value of the inverse of the relative desorbent strength increases). This reduction in desorbent strength, which affects the ability of the desorbent to displace the desired pX product into an extract stream, can have adverse consequences in terms of obtaining pX with a high purity and recovery, particularly in a commercial process for the adsorptive separation of pX operating in a simulated moving bed mode.

These results illustrate the process efficiencies that can be gained from the use of binder-converted compositions in which the converted portion of zeolite X has a Si/Al framework ratio in the range from 1.05 to 1.35, which may be the same or substantially the same as that for the prepared portion of zeolite X. However, zeolite X-precursors such as kaolin clay often have lower Si/Al ratios, for example about 1.0, and therefore normally do not convert to the desired, higher ratio zeolite X.

However, it is possible to modify the procedure in which the zeolite X-precursor is converted to zeolite X, in synthesis of a binder-converted composition, to increase the silica to alumina molar ratio of the converted portion of zeolite X. This may be achieved through the addition of silica source such as colloidal silica sol, silicic acid, sodium silicate, silica gel, or reactive particulate silica (e.g., diatomaceous earth, Hi-Sil, etc.). The silica source can be added during the adsorbent particle forming step, to the caustic digestion step, or both. The amount of silica added is such that the overall reaction mixture of zeolite X-precursor (e.g., meta-kaolin) and the silica source is controlled such that the reaction composition falls into the following range: $Na_2O/SiO_2=0.8-1.5$, $SiO_2/Al_2O_3=2.5-5$, $H_2O/Na_2O=25-60$.

The use of a separate source of silica can therefore allow the preparation of a binder-converted composition in which the Si/Al ratio of both the prepared and converted portions of zeolite X are closely matched (e.g., are both within the range from 1.0 to 1.5, and normally from about 1.05 to 1.35), thereby overcoming the drawbacks discussed above with respect to the use of lower ratio zeolite X in the adsorptive separation of pX. Advantageously, the increase in the silica to alumina molar ratio of the converted portion of zeolite X can also improve the hydrothermal stability of the resulting binder-converted composition.

The relative amounts of the first prepared and second converted portions of zeolite X in the binder-converted composition may be varied. According to some embodiments, the amount of zeolite X-precursor used in the preparation of the formed particle will be in the range from about 5% to about 40% by weight, and preferably from about 10% to about 30% by weight. These ranges therefore also correspond to the amounts of converted zeolite X that is present in representative binder-converted compositions described herein.

Preferably, the binder material content, after conversion to the second zeolite is in a range of from 0 to 3 wt %. In exemplary binder-converted compositions, non-zeolitic material is substantially absent (e.g., is present in the composition generally in an amount of less than about 2% by weight, typically less than 1% by weight, and often less than 0.5% by weight). The absence or substantial absence of non-zeolitic or amorphous material may be confirmed by analysis of the binder-converted composition using X-ray diffraction and/or high resolution scanning electron microscopy (HR-SEM) to verify crystal structure. Macro- and micro-pore structure and distribution may by characterized and confirmed using mercury porosimetry or liquid oxygen adsorption.

Determining LTA Zeolite Content in Zeolite X by XRD

As discussed above, the present invention requires that the X zeolite has a mean diameter not greater than 2.7 μm. Additionally, the present invention also requires a low LTA-containing X zeolite. The LTA zeolite level must either be non-detectable or otherwise have a relative intensity not greater than 0.35, as determined by the XRD method described under the characterization examples below. As discussed more fully below, the relative intensity of the LTA zeolite (relative "LTA intensity") of the sample is determined from the sum of the integrated areas under three LTA-type zeolite peaks with Miller indices of (2 0 0), (4 2 0), and (6 2 2) at 7.27±0.16°, 16.29±0.34° and 24.27±0.50° 2θ, relative to the sum of the same peaks for highly crystalline standard NaA zeolite.

Beyond these three peaks, there are other peaks present in a XRD scan of LTA-type zeolite. However, these three peaks, with Miller indices of (2 0 0), (4 2 0), and (6 2 2) at 7.27±0.16°, 16.29±0.34° and 24.27±0.50° 2θ, tend to have the least overlap or interference from other non-LTA-type zeolite materials and still provide a significant total intensity for the sum of three peak intensities from the Na-exchanged LTA zeolite scan. Furthermore, XRD characterization of the zeolite X sample for its LTA zeolite content must be obtained using a sodium-exchanged form of the zeolite X and the LTA zeolite reference material (i.e., NaA zeolite), respectively.

Accordingly, the relative LTA intensity is calculated as 100 times the quotient of $$\frac{\text{a sample } LTA \text{ XRD intensity for the zeolite } X}{\text{a reference XRD intensity for a } LTA \text{ zeolite reference material consisting essentially of } LTA \text{ zeolite}}$$

wherein the sample LTA XRD intensity for the zeolite X is the sum of the integrated areas under three LTA zeolite peaks with Miller indices of (2 0 0), (4 2 0), and (6 2 2) at 7.27±0.16°, 16.29±0.34° and 24.27±0.50° 2θ and the reference XRD intensity for the LTA zeolite reference material is the sum of the integrated areas under three LTA zeolite peaks with the same Miller indices and related 2θ values.

As can be seen from FIG. 1, the reference material, a Na-exchanged zeolite A, (designated as scan A), provides the three LTA zeolite peaks with their respective Miller indices and 2θ values specified above, which can be used for determining the LTA zeolite content of different sample materials such as, in this case, zeolite X. Scan B of a comparative material, prepared in accordance with the synthesis example (C-1) described below but fully Na-exchanged prior to XRD analysis, indicates the presence of detectable LTA zeolite in a zeolite X having a mean diameter not greater than 2.7 μm, while Scan C of a low-LTA containing X zeolite indicates no detectable LTA zeolite, also fully Na-exchanged prior to XRD analysis.

Figure 2:
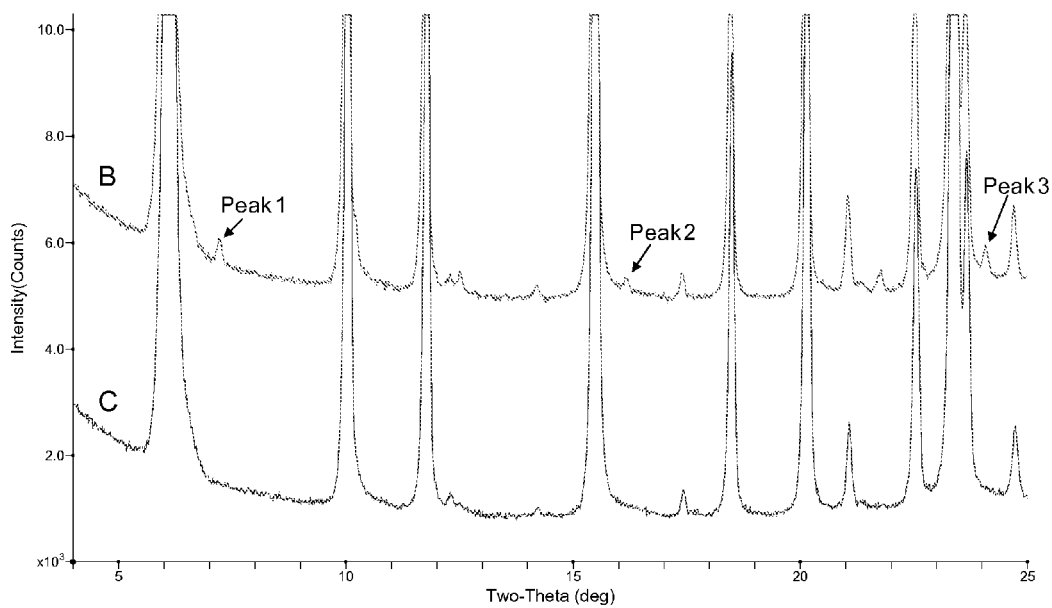
FIG. 2 illustrates the same comparative scans of FIG. 1, but with the Na-exchanged zeolite A reference scan not shown and at 10× magnification so the three LTA zeolite peaks best indicating the presence of LTA zeolite, if any, are more easily observed.

FIG. 2 illustrates the same comparative scans of FIG. 1, but with the Na-exchanged zeolite A reference scan not shown and at 10× magnification so the three LTA zeolite peaks best indicating the presence of LTA zeolite, if any, are more easily observed.

For scan B, related to comparative example C-1, the integrated areas under three LTA zeolite peaks with Miller indices of (2 0 0), (4 2 0), and (6 2 2) at 7.27±0.16°, 16.29±0.34° and 24.27±0.50° 2θ are 5.9, 2.3 and 5.1. So the sum of these three specified peak areas is 13.3. For scan A, related to the Na-exchanged zeolite A reference material, the integrated areas under its peaks with Miller indices of (2 0 0), (4 2 0), and (6 2 2) at 7.27±0.16°, 16.29±0.34° and 24.27±0.50° 2θ are 641.5, 243.1 and 607.4. So, the sum of these three specified peak areas is 1492. Accordingly, the relative LTA intensity for the sample is (13.3/1492)×100=0.89.

Ion-Exchange

The portions first prepared zeolite X and second converted zeolite X in the binder-converted composition may be in their sodium form initially, and the sodium cations may be partially or wholly exchanged by different cations, such as barium, potassium, strontium, and/or calcium, using known techniques. For example, the binder-converted composition, synthesized with zeolite X having at least some of its ion-exchangeable sites in sodium ion form, may be immersed in a barium ion containing solution, or a barium and potassium ion containing solution, at conditions of time and temperature (e.g., about 0.5 to about 10 hours at about 20 to about 125° C.) which can effect ion exchange or replacement of sodium ions with barium and/or potassium ions. Ion-exchange can also be conducted in a column operation according to known techniques, for example by pumping preheated barium chloride/potassium chloride solutions through a column of the adsorbent particles to completely displace the sodium cations of the zeolite X. Filtration of the binder-converted composition, removal from the solution, and re-immersion in a fresh solution (e.g., having the same or different ratios or cations or other types of cations) can be repeated until a desired level of exchange, with the desired types and ratios of cations, is achieved.

Advantageously, the binder-converted composition will have at least 95% or substantially all (e.g., at least 99%) of the zeolite X ion-exchangeable sites exchanged with barium or a combination of barium and potassium. Generally, no other metal ions occupy ion-exchangeable sites of the first prepared of zeolite X or the second converted portion of zeolite X in an amount effective to alter the adsorptive properties of the composition. In one embodiment, the zeolite X of the binder-converted composition will have from about 60% to about 100% of its ion-exchangeable sites exchanged with barium and from about 0% to about 40% of its ion-exchangeable sites exchanged with potassium.

The number of ion-exchangeable sites decreases as the overall Si/Al molar ratio of the zeolite X increases. The overall ratio may be affected by varying the ratio of either or both of the first prepared zeolite X and second converted zeolite X portions. Also, the total number of cations per unit cell decreases as monovalent cations (e.g., K+) are replaced by divalent cations (e.g., $Ba^{+2}$). Within the zeolite X crystal structure, there exist many ion-exchangeable site locations, some of these being in positions outside of the supercages. Overall, the number and locations of cations in the zeolite crystal structure will depend upon the sizes and numbers of the cations present, as well as the Si/Al molar ratio of the zeolite.

Para-Xylene Separation

Separation of pX is carried out by contacting a mixture of pX and at least one other $C_8$ alkylaromatic hydrocarbon with an adsorbent. For example, a feed stream comprising the mixture of $C_8$ alkylaromatic hydrocarbons may be contacted with a bed of the adsorbent in order to selectively adsorb, in an adsorbed phase, the pX, in preference to ortho-xylene (oX), meta-xylene (mX), and ethylbenzene (EB). These other $C_8$ alkylaromatic components of the feed stream may selectively pass through the adsorption zone as a non-adsorbed phase.

Feed streams comprising mixtures of $C_8$ alkylaromatic hydrocarbons can be separated from various refinery process streams (e.g., reformate) and may also contain other compounds, such as $C_9$ alkylaromatic hydrocarbons. In one type of separation process, after the adsorptive capacity of the adsorbent is reached, the feed stream inlet flow to the adsorbent is stopped, and the adsorption zone is then flushed to remove a non-adsorbed phase, initially surrounding the adsorbent, from contact with the adsorbent. The adsorbed phase, enriched in the desired pX, may be thereafter desorbed from the adsorbent pores by treating the adsorbent with a desorbent, normally comprising a cyclic hydrocarbon (e.g., an aromatic ring-containing hydrocarbon) such as toluene, benzene, indan, para-diethylbenzene, 1,4-diisopropylbenzene, or mixtures thereof. The same desorbent is commonly used for both (i) flushing the non-adsorbed phase into a raffinate stream comprising the desorbent and (ii) desorbing the adsorbed phase into an extract stream, also comprising the desorbent. Because the extract stream contains the adsorbed phase, which is enriched in pX, the extract stream will also be enriched in pX, relative to the feed stream, when considered on a desorbent-free basis.

The capacity of the adsorbent for adsorbing a specific volume of pX from a mixture of $C_8$ alkylaromatics, such as a mixture of xylenes (oX, mX and pX) and EB is an important characteristic, as increased capacity makes it possible to reduce the amount of adsorbent needed to separate the pX for a particular charge rate of feed. So increased adsorbent capacity for pX can result in a more efficient separation process provided good initial capacity for the extract component (pX in this case), as well as total adsorbent capacity, should be maintained during actual use in an adsorptive separation process over some economically desirable life.

The rate of exchange of pX with the desorbent can generally be characterized by the width of the peak envelopes at half intensity obtained from plotting the composition of various species in the adsorption zone effluent obtained during a pulse test versus time. The narrower the peak width, the faster the desorption rate. The desorption rate can also be characterized by the distance between the center of the tracer peak envelope and the disappearance of an extract component which has just been desorbed. This distance is time dependent and thus a measure of the volume of desorbent used during this time interval. The tracer is normally a relatively non-adsorbed compound which moves through an adsorbent column faster than the materials to be separated.

Selectivity ($\beta$), for pX with respect to a raffinate component may be characterized by the ratio of the distance between the center of the pX peak envelope and the tracer peak envelope (or other reference point) to the corresponding distance between the center of the raffinate component peak envelope and the tracer peak envelope (or reference point). The selectivity corresponds to the ratio of the two components in the adsorbed phase divided by the ratio of the same two components in the non-adsorbed phase at equilibrium conditions. Selectivity may therefore be calculated from:

$$\text{Selectivity} = (\text{vol-\% } C_A/\text{vol-\% } D_A)/(\text{vol-\% } C_U/\text{vol-\% } D_U)$$

where C and D are two components of the feed mixture represented in weight percent and the subscripts A and U represent the adsorbed and non-adsorbed phases, respectively. The equilibrium conditions are determined when the feed passing over a bed of adsorbent does not change composition, in other words, when there is no net transfer of material occurring between the non-adsorbed and adsorbed phases. In the equation above, a selectivity larger than 1.0 indicates preferential adsorption of component C within the adsorbent. Conversely, a selectivity less than 1.0 would indicate that component D is preferentially adsorbed leaving an non-adsorbed phase richer in component C and an adsorbed phase richer in component D.

For a selectivity of two components approaching 1.0, there is no preferential adsorption of one component by the adsorbent with respect to the other (i.e., they are both adsorbed to about the same degree with respect to each other). As selectivity deviates from 1.0, there is an increasingly preferential adsorption by the adsorbent for one component with respect to the other. Selectivity can be expressed not only for one feed stream compound relative to another (e.g., pX to mX selectivity) but can also be expressed between any feed stream compound and the desorbent (e.g., pX to para-diethylbenzene selectivity).

While separation of an extract component from a raffinate component is theoretically possible when the adsorbent selectivity for pX with respect to the raffinate component is only slightly greater than 1, it is preferred that this selectivity is at least 2 for process economic considerations. Generally, the higher the selectivity, the easier the adsorptive separation is to perform. Higher selectivities allow use of smaller amounts of adsorbent to obtain the same productivity (e.g., pX recovery) with an adsorbent having comparatively lower selectivity for the same component in mixture (e.g., pX from oX, mX and EB).

The desorbent for an adsorptive separation process must be judiciously selected to satisfy several criteria. The desorbent should ideally have sufficient strength (i.e., be adsorbed strongly enough) to displace pX from the adsorbent at a reasonable mass flow rate, without being so strongly adsorbed as to prevent pX from displacing the desorbent in a following adsorption cycle. In terms of the selectivity, it is preferred that the adsorbent be more selective for the pX with respect to a raffinate component than it is for the desorbent with respect to the raffinate component.

A performance parameter to be considered for the desorbent is therefore its rate of exchange for pX in the feed or, in other words, the relative rate of desorption of pX. This parameter relates directly to the amount of desorbent that must be used in an adsorptive separation process to desorb pX from the adsorbent. Faster rates of exchange reduce the amount of desorbent needed and therefore improve operating efficiency with larger desorbent-containing process streams, including the separation and recycle of desorbent from these streams. A desorbent selectivity of 1 or slightly lower with respect to an extract component helps ensure that all the pX is desorbed with a reasonable flow rate of desorbent, and also that extract components can displace desorbent in a subsequent adsorption step. One way of measuring selectivity can be by a "pulse test" described below.

EXAMPLES

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

SYNTHESIS EXAMPLES

Example S-1

Seed Crystals

An aluminate solution is prepared by mixing 755 g sodium hydroxide (50% NaOH), 425 g alumina trihydrate and 320 g water. The mixture is heated to 230° F. and held for 15 minutes, then cooled to 120° F.

225 g aluminate solution is mixed with 1035 g water, 643 g sodium hydroxide (50% NaOH) and 1298 g sodium silicate. After mixing, the batch is allowed to age for 72 hours to produce zeolite seed crystals.

Example S-2

Zeolite X

An aluminate solution is prepared by mixing 970 g sodium hydroxide (50% NaOH), 313 g alumina trihydrate and 418 g water. The mixture is heated to 230° F.

559 g aluminate solution is mixed with 0.35 g seed crystals prepared according to Example S-1, 1744 g water, and 439 g sodium silicate.

The solution is then aged for 3.5 hours. The resulting crystals are filtered from the solution and dried. The crystals are analyzed by XRD and ICP and determined to be zeolite X with a Si/Al framework molar ratio of 1.275. The particle size is determined to be 1.7 μm by sedigraph analysis, according to the method described below.

Example S-3

Binder-Converted Zeolite X Composition

A 860 g portion of the zeolite X prepared according to Example S-2 is agglomerated with 140 g kaolin (ASP 400™ obtained from BASF), 20 g cornstarch and 20 g carboxymethyl cellulose (obtained from BASF) an appropriate amount of water. The mixture is extruded and the extrudates are dried and activated at 650° C. for 4 hours under dry air. The extrudates are then meshed to an average size of 0.5 mm.

A 100 g portion of the agglomerates is then immersed in 580 g of NaOH solution with a concentration of 2.4% for binder conversion. The binder conversion temperature is 80-100° C. and lasts for 6 hrs.

COMPARATIVE EXAMPLES

Example C-1

Comparative Zeolite X

Comparative zeolite X is prepared according to Example S-2, but using 825 g sodium silicate and 0.7 g seed crystals prepared according to Example S-1.

The crystals are analyzed by XRD and ICP and determined to be zeolite X with a Si/Al framework molar ratio of 1.225. The particle size is determined to be 1.7 µm by sedigraph analysis, according to the method described below.

Example C-2

Comparative Zeolite X

Another comparative zeolite X is prepared by first forming an aluminate solution by mixing 1058 g liquid sodium aluminate, 160 g sodium hydroxide (50% NaOH) and 432 g water. Then, 523 g aluminate solution is mixed with 454 g water and 451 g sodium silicate.

The solution is aged for 2.3 hours and then crystallized for 5 hours. The crystals are filtered. The crystals are analyzed by XRD and ICP and determined to be zeolite X with a Si/Al framework molar ratio of 1.25. The particle size is determined to be 3.8 µm by sedigraph analysis, according to the method described below.

POST-SYNTHESIS TREATMENT EXAMPLES

Example T-1

A sample prepared according to Example S-3 is ion-exchanged with a mixture of 12 wt % BaCl and 1 wt % KCl solution. The ion-exchange solution to solid ratio by mass is 21 to 1. The ion-exchange is carried out in a column at 95° C. for 2 hours. After ion-exchange is completed, the column is drained and the solid material is then washed with water until the chloride level is below 0.05 wt %. The washed sample is then dried in a Blue M oven at 250° C. under dry air flow for 1 hour. The material obtained has an LOI of 5.7-5.8 wt %.

The water content of the adsorbent is expressed herein in terms of the recognized LOI test at 900° C. The LOI test is described in UOP Test Method No. UOP954-03 (available through ASTM International, 100 Barr Harbor Drive, PO Box C700, West Conshohocken, Pa., 19428-2959 USA).

Example T-2

A comparative sample prepared according to Example C-1 is ion-exchanged in the same manner as Example T-1.

CHARACTERIZATION EXAMPLES

Example CH-1

X-Ray Diffraction (XRD) for Determining Relative Amount of LTA Zeolite

The relative amount of LTA zeolite in the zeolite of this invention can be determined by XRD analysis. The x-ray patterns presented in the following examples were obtained using standard XRD techniques.

The sample is ground to a powder (typically 150 mesh or less), then placed in a 53% relative humidity chamber containing a saturated solution of $CaNO_3$ at least overnight (~15 hours). An approximately 1 gram sample of the equilibrated powder is spread onto a XRD sample holder and placed into the XRD instrument and scanned using parameters of 5.0° to 25.0° 2θ with a 0.02° step size and 10 second per step counting time. The XRD instrument is a Scintag XDS2000 instrument or functional equivalent equipped with a copper x-ray tube. The XRD instrument is run at settings of 45 kV and 35 mA. The humidity in the instrument is maintained at 53% humidity.

The relative amount of LTA zeolite in the sample is determined from the sum of the integrated areas under the three LTA zeolite peaks with Miller indices of (2 0 0), (4 2 0), and (6 2 2) at 7.27±0.16°, 16.29±0.34° and 24.27±0.50° 2θ, relative to the sum of the same peaks for highly crystalline standard NaA zeolite. The Miller indices, (h k l), designate which LTA-type zeolite peaks are to be included in the integration procedure and are related to the peak positions by the equation $$\lambda = (2a_{NaLTA} \sin(\theta_{hkl}))/(h^2+k^2+l^2)^{1/2}$$

where λ is the x-ray wavelength (1.54059 Å for CuKα radiation), $a_{NaLTA}$ is the NaA zeolite lattice parameter of 23.8 to 24.8 Å depending on Si/Al ratio, and $\theta_{hkl}$ is one-half the diffraction angle for the peak with Miller indices, (h k l).

Example CH-2

Sedigraph Analysis

Zeolite particle size is measured by a Micromeritics Sedigraph 5120 Particle Size Analysis System. The Sedigraph 5120 is completely automatic and the operation of this unit is in accordance with the Operators Manual provided.

A zeolite sample is first dispersed in deionized water (2.8 gram of zeolite/50 gram of D.I. water). The sample is then transferred to the Sedigraph unit. From this equipment, the particle size distribution of zeolite particles is obtained on a weight average basis. For example, a D50 or a D90 of the particle size distribution can be obtained. D50 indicates a diameter for which 50 wt. % of the particles are below the specified diameter, while D90 indicates a diameter for which 90 wt. % of the particles are below the specified diameter. Accordingly, D50 is also known as the mean diameter.

Example CH-3

Pulse Test for Selectivity Performance

A "pulse test" is used to test adsorptive capacity, selectivity, resolution, and exchange rate. The pulse test apparatus includes a tubular adsorbent chamber of approximately 70 cubic centimeters (cc) in volume and having inlet and outlet portions at opposite ends of the chamber. The chamber is equipped to allow operation at constant, predetermined temperature and pressure. Quantitative and qualitative analytical equipment such as refractometers, polarimeters and chromatographs can be attached to an outlet line of the chamber and used to detect quantitatively and/or determine qualitatively one or more components in the effluent stream leaving the adsorbent chamber.

During a pulse test, the adsorbent is first filled to equilibrium with a particular desorbent by passing the desorbent through the adsorbent chamber. A small volume or pulse of the feed mixture, which may be diluted with desorbent, is injected by switching the desorbent flow to the feed sample loop at time zero. Desorbent flow is resumed, and the feed mixture components are eluted as in a liquid-solid chromatographic operation. The effluent can be analyzed on-stream or, alternatively, effluent samples can be collected periodically and analyzed separately (off-line) and traces of the envelopes of corresponding component peaks plotted in terms of component concentration versus quantity of effluent.

Information derived from the pulse test can be used to determine adsorbent void volume, retention volume for pX or a raffinate component, selectivity for one component with respect to the other, stage time, the resolution between the components, and the rate of desorption of pX by the desorbent. The retention volume of pX or a raffinate component may be determined from the distance between the center of the peak envelope of pX or a raffinate component and the peak envelope of a tracer component or some other known reference point. It is expressed in terms of the volume in cubic centimeters of desorbent pumped during the time interval corresponding to the distance between the peak envelopes.

A sample prepared according to Example S-3 and ion-exchanged according to Example T-1 is evaluated in the adsorptive separation of pX. A comparative sample prepared according to Example C-1 and ion-exchanged according to Example T-2 is also evaluated.

A standard pulse test as described above was performed by first loading the adsorbent in a 70 cm³ column under the desorbent para-diethylbenzene (pDEB). A feed pulse containing equal quantities of EB and each of the three xylene isomers, together with a normal nonane (n-C₉) tracer, is injected. Pulse tests are performed at various column temperatures in the range from 121° C. to 177° C. (250° F. to 350° F.) to examine the effect of temperature on selectivity. The pX selectivities were determined from the component peaks obtained from each of these pulse tests, and the results at 150° C. are shown in Table CH-1 below.

Example CH-4

Capacity Testing

A sample prepared according to Example S-3 and ion-exchanged according to Example T-1 is evaluated for its capacity in the adsorptive separation of pX. A comparative sample prepared according to Example C-1 and ion-exchanged according to Example T-2 is also evaluated.

A column containing 70 cm³ of the adsorbent, initially loaded under pDEB, is charged with a sample feed mixture containing oX, mX, pX, and EB. Breakthrough tests are performed at a column temperature of 150° C. to determine the adsorbent's capacity (cm³) and pX/pDEB selectivity (as defined above) at LOI=5.7-5.8%, and the results are shown in Table CH-1 below.

TABLE CH-1

| Sample | P/E | P/M | P/O | Capacity (cm³) | pX/pDEB | F | D/F |
|---|---|---|---|---|---|---|---|
| S-3/T-1 | 1.8 | 5.4 | 4.8 | 12.5 | 1.24 | 101 | 0.97 |
| C-1/T-2 | 1.8 | 5.4 | 5.0 | 12.0 | 1.39 | 100 | 1.06 |

Based on the selectivity and capacity results, simulated moving bed (SMB) modeling analysis is used to estimate the feed throughput and desorbent to feed (D/F) requirement in a commercial pX separation process. The results comparison is also shown in Table CH-1. The feed rate increase of S-3/T-1 over C-1/T-2 is 1%, whereas the desorbent requirement is reduced to 92%. This represents significant reduction in the amount of desorbent required to efficiently operate a pX separation process. D/F is based on mass flow ratio. Here we assume C-1/T-2 case is the base case at 100.

The invention claimed is:

1. A zeolitic binder-converted composition comprising:
   a. a zeolite X composition having at least a first zeolite X having a mean diameter not greater than 2.7 microns, as determined by sedigraph analysis, and a second zeolite X, wherein the second zeolite X is obtained by converting a binder material to the second zeolite X and the binder material is in a range from 5 to 30 wt % of the zeolite X composition, and
   b. an unconverted binder material content, after conversion to the second zeolite X is complete, in a range from 0 to 3 wt % of the zeolite X composition;
   wherein the zeolite X composition has
   i. an average Si/Al framework mole ratio in a range from 1.0 to 1.5, wherein the Si/Al framework mole ratio of the first zeolite and the second zeolite are different; and
   ii. a relative LTA intensity not greater than 1.0, as determined by a x-ray diffraction (XRD) method using a source of CuKα radiation to obtain XRD intensities in range from 5° to 25° 2θ,
      wherein, the relative LTA intensity is calculated as 100 times the quotient of $$\frac{\text{a sample } LTA \text{ XRD intensity for the zeolite } X}{\text{a reference } XRD \text{ intensity for a } LTA \text{ zeolite reference material consisting essentially of } LTA \text{ zeolite}}$$

wherein,
      1. the sample LTA XRD intensity of the zeolite X composition is the sum of the intensities for each LTA peak with Miller indices of (2 0 0), (4 2 0), and (6 2 2) at 7.27 ±0.16°, 16.29 ±0.34° and 24.27 ±0.50° 2θ, and
      2. the reference XRD intensity of the LTA-type zeolite reference material is the sum of the intensities for each LTA peak with Miller indices of (2 0 0), (4 2 0), and (6 2 2) at 7.27 ±0.16°, 16.29 ±0.34° and 24.27 ±0.50° 2θ,
      wherein,
         the sample LTA XRD intensity and the reference XRD intensity are each
         a. obtained for a sodium-exchanged form of the zeolite X composition and the LTA-type zeolite reference material, respectively, and
         b. equilibrated at 50% relative humidity.

2. The zeolitic binder-converted composition of claim 1 wherein the unconverted binder material content, after conversion to the second zeolite X is complete, is in a range from 0 to 2 wt % of the zeolite X composition.

3. The zeolitic binder-converted composition of claim 1 wherein the average unit cell size of the zeolite X composition is in a range from 24.99 Å to 24.95 angstroms, as determined by XRD of a Na-exchanged form of the zeolite X composition equilibrated at 50% relative humidity.

4. The zeolitic binder-converted composition of claim 1 wherein the average unit cell size of the zeolite X composition is in a range from 24.985 Å to 24.955 angstroms, as determined by XRD of a Na-exchanged form of the zeolite X composition equilibrated at 50% relative humidity.

5. The zeolitic binder-converted composition of claim 1 wherein the average Si/Al framework mole ratio of the zeolite X composition is in a range from 1.15 to 1.35.

6. The zeolitic binder-converted composition of claim 1 wherein the LTA intensity of the zeolite X composition is not greater than 0.8.

7. The zeolitic binder-converted composition of claim 1 wherein the zeolite X is ion-exchanged with barium, potassium, and combinations thereof.

* * * * *